(12) United States Patent
Clements (10) Patent No.: US 9,958,354 B2
(45) Date of Patent: May 1, 2018

(54) INTEGRITY TESTING (71) Applicant: GE Oil & Gas UK Limited, Bristol (GB)

(72) Inventor: Richard Clements, Durham (GB)

(73) Assignee: GE Oil & Gas UK Limited, Bristol (GB)

( * ) Notice: Subject to any disclaimer, the term of this patent is extended or adjusted under 35 U.S.C. 154(b) by 567 days.

(21) Appl. No.: 14/108,832

(22) Filed: Dec. 17, 2013

(65) Prior Publication Data

US 2014/0165709 A1 Jun. 19, 2014

(30) Foreign Application Priority Data

Dec. 18, 2012 (EP) .................................... 12197855

(51) Int. Cl.
*F16L 11/08* (2006.01)
*G01M 5/00* (2006.01)
*G01N 3/12* (2006.01)

(52) U.S. Cl.
CPC ........ *G01M 5/0025* (2013.01); *G01M 5/0075* (2013.01); *G01N 3/12* (2013.01); *F16L 11/083* (2013.01); *G01N 2203/0244* (2013.01); *G01N 2203/0274* (2013.01); *G01N 2203/0664* (2013.01)

(58) Field of Classification Search
CPC ....... B29C 66/71; B29C 63/346; B29C 65/02; B29C 66/5344; B29C 66/55; B29C 66/73116; B29K 2027/18; B29K 2027/12; F16L 33/01; F16L 11/085; F16L 11/12; F16L 2011/047; F16L 2101/30; F16L 2201/44
See application file for complete search history.

(56) References Cited

U.S. PATENT DOCUMENTS

| 5,514,312 A * | 5/1996 | Hardy | F16L 11/087 264/101 |
|---|---|---|---|
| 5,918,641 A * | 7/1999 | Hardy | F16L 11/087 138/132 |
| 2006/0011249 A1* | 1/2006 | Arima | F16L 11/085 138/109 |
| 2010/0068986 A1* | 3/2010 | Eccleston | F16L 11/12 454/339 |

(Continued)

FOREIGN PATENT DOCUMENTS

| CN | 101839797 | 9/2010 |
|---|---|---|
| CN | 102262018 | 11/2011 |

(Continued)

OTHER PUBLICATIONS

Australian Patent Examination Report dated Jul. 23, 2014 in Application No. No. 2013260663.

(Continued)

*Primary Examiner* — Randy Gibson
*Assistant Examiner* — Gedeon M Kidanu
(74) *Attorney, Agent, or Firm* — Knobbe Martens Olson & Bear LLP (57) ABSTRACT

A method and apparatus are disclosed for testing one or more layers of a flexible pipe. The method includes the steps of applying a test cycle to a flexible pipe and simultaneously applying the same test cycle to a tubular test layer connected in an in-line configuration with the flexible pipe.

16 Claims, 5 Drawing Sheets

(56) References Cited

U.S. PATENT DOCUMENTS

| | | | | |
|---|---|---|---|---|
| 2011/0006515 A1* | 1/2011 | Yanik | ............ | B29C 63/346 |
| | | | | 285/239 |
| 2011/0068572 A1* | 3/2011 | Nacsa | ............ | F16L 33/01 |
| | | | | 285/256 |
| 2011/0229271 A1* | 9/2011 | Clements | ............ | F16L 33/01 |
| | | | | 405/224.2 |
| 2012/0222770 A1* | 9/2012 | Kristiansen | ............ | F16L 11/08 |
| | | | | 138/103 |
| 2013/0014849 A1* | 1/2013 | Glejbol | ............ | F16L 11/083 |
| | | | | 138/137 |
| 2013/0125655 A1* | 5/2013 | Klopffer | ............ | F16L 11/083 |
| | | | | 73/592 |

FOREIGN PATENT DOCUMENTS

| | | |
|---|---|---|
| FR | 2962548 | 8/2012 |
| GB | 2220242 A1 | 1/1990 |
| WO | WO 2011/120525 | 10/2011 |
| WO | WO 2012/004508 | 1/2012 |

OTHER PUBLICATIONS

European Search Report dated May 16, 2013 in EP Application No. No. 12197855.5.
Wellstream Flexsteel Flexible Steel Pipe Technical, Operating, and Maintenance Manual, WSI Eng. Doc. No. R092E004, Revision 05, Nov. 13, 2006.

\* cited by examiner

INTEGRITY TESTING

BACKGROUND

The present invention relates to a method and apparatus for testing flexible pipes. In particular, but not exclusively, the present invention relates to a method of applying a conditioning and/or test cycle to a flexible pipe and simultaneously applying the same cycle to a specimen connected in an in-line configuration with the flexible pipe. The specimen includes one or more layers previously removed from the body of the flexible pipe and can subsequently be disconnected from the pipe. The layers in the specimen can then be analysed to determine any potential effect of the conditioning or testing on the flexible pipe (which itself remains intact).

Traditionally flexible pipe has been utilised to transport production fluids, such as oil and/or gas and/or water from one location to another. Flexible pipe has been found to be useful in connecting a sub-sea location to a sea-level location. Flexible pipe has generally been formed as an assembly of flexible pipe body and one or more end fittings. The pipe body is conventionally formed as a combination of layered materials that form a pressure-containing conduit. The pipe structure allows large deflections in use without causing bending stresses that impair the pipe's functionality over its lifetime. The pipe body is generally built up as a combined structure including tubular metallic and polymer layers which are typically unbonded.

Such unbonded flexible pipes have been used for deep water (less than 3300 feet (1005.84 meters)) and ultra-deep water (greater than 3300 feet (1005.84 meters)) developments. Of course flexible pipe may also be used for shallow water applications (for example, less than around 500 meters depth) or even for on-shore (overland) applications.

Flexible pipes often incorporate one or more polymer layers, such as PVDF (polyvinylidene fluoride) that may be formed by extrusion. Most polymers have a certain maximum allowable strain above which the risk of damage to the material is much greater. In flexible pipes where a polymer layer lies adjacent an armour layer (such as a polymer barrier layer located adjacent a metallic pressure armour layer), the polymer layer may be subjected to quite severe non-uniform, highly localised strain. This is because an armour layer is usually formed from interlocking wires of certain cross-section and there are certain gaps between adjacent windings. The polymer layer tends to deform and creep into those gaps when under pressure.

The application of internal pressure to the pipe (i.e. which can occur when an inner bore is pressurised) produces radial expansion in all layers and under such circumstances a polymer may undergo deformation and tend to creep into gaps of an overlying armour layer. At high pressures (for example, about around 8000 psi/55 MPa or more), the resultant strain distribution within the polymer can be highly localised at the areas around the gaps and the polymer material may deform by cavitation rather than plastic flow. This can in turn result in the formation of micro-crazing or micro-cracking on the radially inner surface of the polymer layer. During any subsequent loading (such as the loading experienced during normal use in transporting production fluids) this micro-crazing may then extend to form longer/deeper cracks throughout the polymer layer. This increases the risk of failure of the polymer layer and may ultimately lead to loss of pressure containment having an adverse effect on the lifetime of a flexible pipe.

In order to ensure there is little or no risk of such micro-crazing or micro-cracking and in accordance with industry regulations, all flexible pipe structures must undergo a factory acceptance test (FAT) subsequent to manufacture and prior to delivery. This involves pressurising a manufactured pipe bore with a fluid, such as water, at 1.5 times the usual pressure expected during use. The water is thus a pressurising medium. The FAT is required by industry standards to be 1.5 times the design pressure of the pipe and this pressure is typically maintained for a minimum of 24 hours. This is typically the highest and most severe pressure cycle that any flexible pipe will ever experience in its lifetime. A successful subsequent evaluation identifying no crazing on a test sample from the same production run experiencing the same pressure cycle thus gives evidence to a potential client that a flexible pipe itself has been manufactured in an acceptable manner. Conventionally such testing has been carried out on a flexible pipe and then parts of the flexible pipe cut through destructively and subsequently analysed. This is a time consuming and costly process since a flexible pipe must first be manufactured including terminating ends of pipe body with end fittings. At least one of these end fittings must then be removed to provide access to part of the pipe which can be removed and used as a test sample. The remainder flexible pipe body and end fitting must then be re-sealed with a new end fitting. Apart from being a time consuming and costly process this is also prone to error and the resultant flexible pipe is not exactly the same as that tested.

It is an aim of the present invention to at least partly mitigate the above-mentioned problems.

It is an aim of certain embodiments of the present invention to provide an in-line test method in which a test piece including one or more tubular test layers can be provided in an in-line configuration with a flexible pipe.

It is an aim of certain embodiments of the present invention to provide an-line conditioning method in which a conditioning piece including one or more tubular conditioning layers can be provided in an in-line configuration with a flexible pipe.

It is an aim of certain embodiments of the present invention to provide a method and apparatus for probing a layer of a flexible pipe. That is to say, applying a conditioning cycle and/or a test cycle to a flexible pipe and specimen connected in an in-line configuration with the flexible pipe simultaneously.

It is an aim of certain embodiments of the present invention to enable a flexible pipe to be manufactured and tested intact without subsequently having to destroy part or parts of the flexible pipe and thereafter re-fit an end fitting.

It is an aim of certain embodiments of the present invention to provide apparatus for testing a non-metallic layer used in flexible pipe body.

SUMMARY

According to a first aspect of the present invention there is provided a method of probing a layer of a flexible pipe, comprising the steps of:
  applying a probe cycle to a flexible pipe; and
  simultaneously applying the probe cycle to a tubular probe layer connected in an in-line configuration with said flexible pipe.

Aptly, the method of probing comprises a method of testing and the probe cycle comprises a test cycle and the probe layer comprises a test layer.

Aptly, the method of probing comprises a method of conditioning and said probe cycle comprises a conditioning cycle and said probe layer comprises a conditioning layer.

Aptly the method further comprises the steps of, prior to applying the test cycle, applying a conditioning treatment cycle to the flexible pipe; and
  simultaneously applying the treatment cycle to the test layer connected in said in-line configuration.

Aptly the method further comprises the steps of:
  subsequent to application of the test cycle, disconnecting the test layer from the flexible pipe leaving the flexible pipe intact; and
  determining if at least one characteristic associated with the test layer satisfies at least one pre-determined condition.

Aptly the method further comprises the steps of providing the test layer by cutting off an end section from manufactured flexible pipe body and providing the cut off end section for testing.

Aptly the method further includes the steps of providing the test layer by, during manufacture of the flexible pipe body, manufacturing at least one layer having an excess length, cutting off the excess length of said one layer and providing the cut off length for testing.

Aptly the method further comprises the steps of applying the test cycle by urging fluid having a pressure and/or temperature elevated with respect to an ambient pressure and/or temperature along an inner bore of the flexible pipe and the test layer for a pre-determined period of time.

Aptly the step of applying a test cycle comprises applying a factory acceptance test (FAT) to the flexible pipe.

Aptly the elevated pressure is about around 1.5 times a design pressure of the flexible pipe.

Aptly the method further comprises, when the test layer is a polymer layer, locating a pressure armour simulation element over the test layer prior to connection of the test layer in said in-line configuration with the flexible pipe.

Aptly when the test layer is connected in-line with the flexible pipe the method comprises the steps of:
  sealing a first end of the tubular test layer to a first connector;
  sealing a remaining end of the test layer to a further connector; and
  connecting a one of the first and further connectors to an end fitting of the flexible pipe.

Aptly the test layer is sealed to the first and a further connector by a method comprising the steps of:
  locating a first and further inner collar member at a respective end of an inner bore region of the test layer;
  locating a first and further sealing ring over the test layer at a respective first and further end of the test layer; and
  securing the first and further connectors to an intermediate connector body.

Aptly the method further comprises energising the first and further sealing rings as the first and further connectors are secured to the intermediate connector body.

Aptly the method further comprises sealing each connector to the intermediate body with at least one gasket ring.

According to a second aspect of the present invention there is provided apparatus for probing a layer of a flexible pipe, comprising:
  a tubular probe layer; and
  a rigid simulation element comprising a substantially cylindrical body extending over the probe layer and providing at least one inset region at an interface between the probe layer and the simulation element.

Aptly each inset region has a dimension and shape that at least approximates to a corresponding dimension and shape of a concave region between adjacent windings of a carcass layer.

Aptly the simulation element is a substantially hollow cylindrical body having a smooth outer surface and inner surface that is smooth remote from each inset region.

Aptly an inner diameter of the simulation element substantially matches an outer diameter of the tubular test layer.

Aptly the at least one inset region comprises a helical groove that extends along an inner surface of the simulation element.

Aptly the at least one inset region comprises a plurality of ring-like grooves spaced apart in a side-by-side relationship along an inner surface of the simulation element.

Aptly the apparatus further comprises:
  a first and further flange connector each having an end that is mateable with an end fitting of a flexible pipe;
  a first and further collar member, each locatable in a respective end of an inner bore region of the test layer;
  an intermediate connector connectable to the first and further flange; and
  a first and further seal that each seal a respective end of the test layer to a respective flange connector when the first and further flange connectors are connected to the intermediate connector.

According to a third aspect of the present invention there is provided an apparatus constructed and arranged substantially as herein described with reference to the accompanying drawings.

According to a fourth aspect of the present invention there is provided a method substantially as herein described with reference to the accompanying drawings.

Certain embodiments of the present invention allow a flexible pipe and a specimen piece to be probed simultaneously. That is to say, a test cycle can be simultaneously applied to a flexible pipe and a specimen or a conditioning treatment cycle can be simultaneously applied to a pipe and a specimen or a conditioning treatment cycle can be simultaneously applied to a flexible pipe and specimen piece and then simultaneously a test cycle applied. Probing the layers of flexible pipe and specimen layer is thus an exploratory action by which the flexible pipe and specimen layer can be investigated to obtain information.

Certain embodiments of the present invention allow a flexible pipe to be tested intact and sections of one or more of the layers used in the flexible pipe to be mounted as a test specimen to be simultaneously tested. These layers from the test sample may subsequently be detached from the flexible pipe and analysed to see if the pipe itself is likely to be acceptable. A successful evaluation for crazing on a test sample from the same production run and experiencing the same pressure cycle will help provide categoric evidence to an end user that the pipe itself is acceptable. This obviates the need to cut and examine a completed and factory acceptance tested (FAT) section of pipe or perform a second test off-line in a different set-up.

Certain embodiments of the present invention provide the ability to test a section of the same pipe or a stripped down section of the same pipe or even just a polymer layer from the same production run as that of a flexible pipe itself. The test specimen and flexible pipe itself experience exactly the same pressure test, and therefore the same pressure cycle regime. The test specimen thereafter can thereafter be destructively tested.

Certain embodiments of the present invention provide a mounting system in which one or more layers from a flexible pipe can be mounted and then connected in an in-line configuration with a flexible pipe. This avoids the need for the sample piece to be terminated in end fittings of the type which are utilised for the flexible pipe itself.

DESCRIPTION OF DRAWINGS

Embodiments of the present invention will now be described hereinafter, by way of example only, with reference to the accompanying drawings in which.

In the drawings like reference numerals refer to like parts.

DETAILED DESCRIPTION

Figure 1:
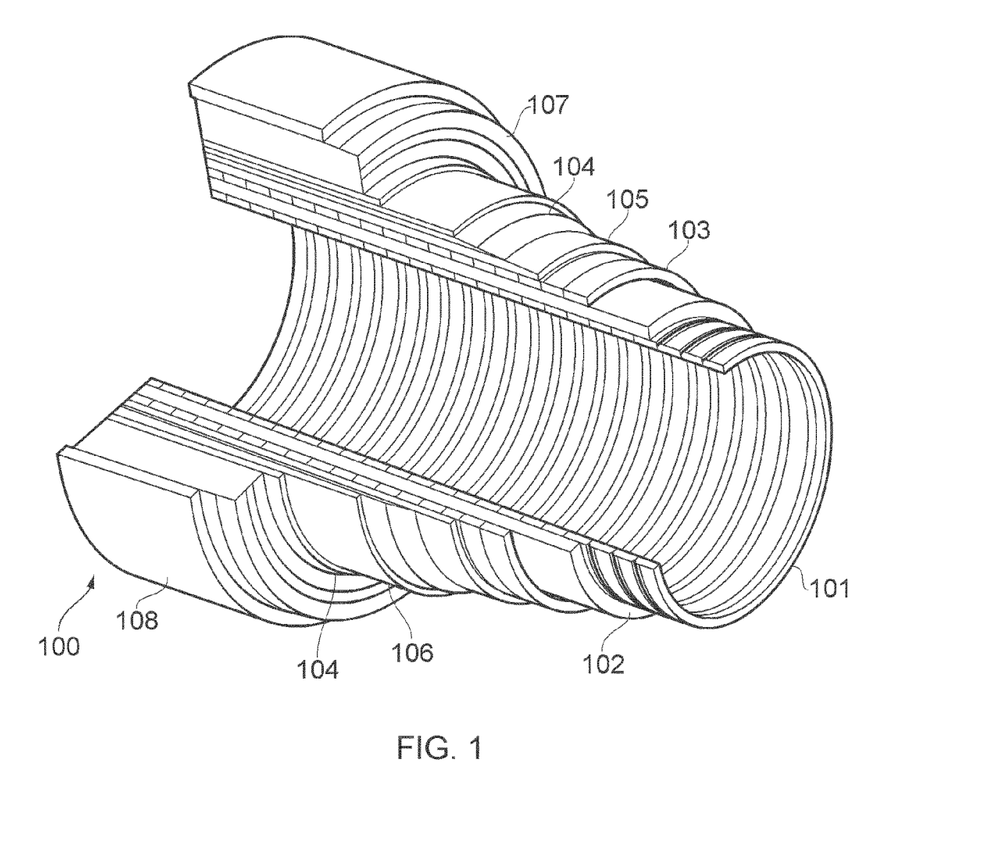
FIG. 1 illustrates flexible pipe body.

Throughout this description, reference will be made to a flexible pipe. It will be understood that a flexible pipe is an assembly of a portion of pipe body and one or more end fittings in each of which a respective end of the pipe body is terminated. FIG. 1 illustrates how pipe body 100 is formed in accordance with an embodiment of the present invention from a combination of layered materials that form a pressure-containing conduit. Although a number of particular layers are illustrated in FIG. 1, it is to be understood that the present invention is broadly applicable to coaxial pipe body structures including one or more layers manufactured from a variety of possible materials. It is to be further noted that the layer thicknesses are shown for illustrative purposes only.

As illustrated in FIG. 1, a pipe body includes an optional innermost carcass layer 101. The carcass provides an interlocked construction that can be used as the innermost layer to prevent, totally or partially, collapse of an internal pressure sheath 102 due to pipe decompression, external pressure, and/or tensile armour pressure and mechanical crushing loads. It will be appreciated that certain embodiments of the present invention are applicable to 'smooth bore' operations (i.e. without a carcass) as well as such 'rough bore' applications (with a carcass).

The internal pressure sheath 102 acts as a fluid retaining layer and comprises a polymer layer than ensures internal fluid integrity. It is to be understood that this layer may itself comprise a number of sub-layers. It will be appreciated that when the optional carcass layer is utilised the internal pressure sheath is often referred to by those skilled in the art as a barrier layer. In operation without such a carcass (so-called smooth bore operation) the internal pressure sheath may be referred to as a liner.

An optional pressure armour layer 103 is a structural layer with elements having a lay angle close to 90° that increases the resistance of the flexible pipe to internal and external pressure and mechanical crushing loads. The layer also structurally supports the internal pressure sheath, and is typically f an interlocked construction.

The flexible pipe body also includes an optional first tensile armour layer 105 and optional second tensile armour layer 106. Each tensile armour layer is a structural layer with a lay angle typically between 10° and 55°. Each layer is used to sustain tensile loads and internal pressure. The tensile armour layers are often counter-wound in pairs.

The flexible pipe body shown also includes optional layers 104 of tape which each help contain underlying layers and may act as a sacrificial wear layer to help prevent abrasion between adjacent layers.

The flexible pipe body also typically includes optional layers of insulation 107 and an outer sheath 108, which comprises a polymer layer used to help protect the pipe against penetration of seawater and other external environments, corrosion, abrasion and mechanical damage.

Each flexible pipe comprises at least one portion, sometimes referred to as a segment or section of pipe body 100 together with an end fitting located at at least one end of the flexible pipe. An end fitting provides a mechanical device which forms the transition between the flexible pipe body and a connector. The different pipe layers as shown, for example, in FIG. 1, are terminated in the end fitting in such a way as to transfer the load between the flexible pipe and the connector.

Figure 2:
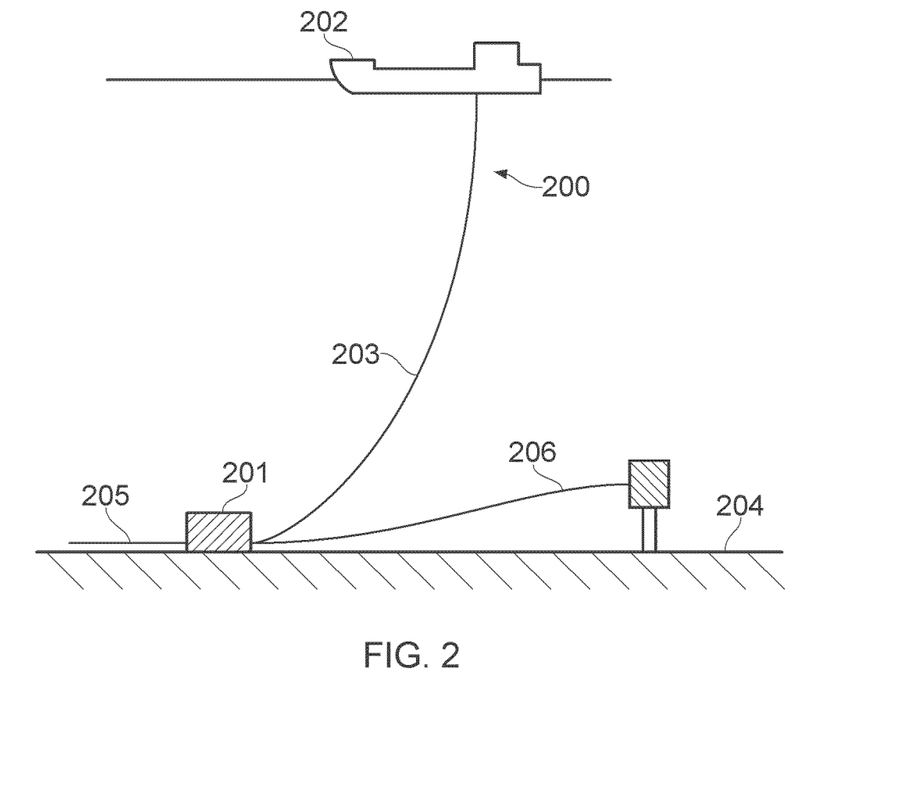
FIG. 2 illustrates uses of a flexible pipe.

FIG. 2 illustrates a riser assembly 200 suitable for transporting production fluid such as oil and/or gas and/or water from a sub-sea location 201 to a floating facility 202. For example, in FIG. 2 the sub-sea location 201 includes an end of a sub-sea flow line. The flexible flow line 205 comprises a flexible pipe, wholly or in part, resting on the sea floor 204 or buried below the sea floor and used in a static application. The floating facility may be provided by a platform and/or buoy or, as illustrated in FIG. 2, a ship. The riser assembly 200 is provided as a flexible riser, that is to say a flexible pipe 203 connecting the ship to the sea floor installation. The flexible pipe may be a single section or segments of flexible pipe body with end fittings connected end-to-end.

It will be appreciated that there are different types of riser, as is well-known by those skilled in the art. Embodiments of the present invention may be used with any type of riser, such as a freely suspended (free, catenary riser), a riser restrained to some extent (buoys, chains), totally restrained riser or enclosed in a tube (I or J tubes). FIG. 2 also helps illustrate how portions of flexible pipe can optionally be utilised as a flow line 205 or jumper 206.

Figure 3:
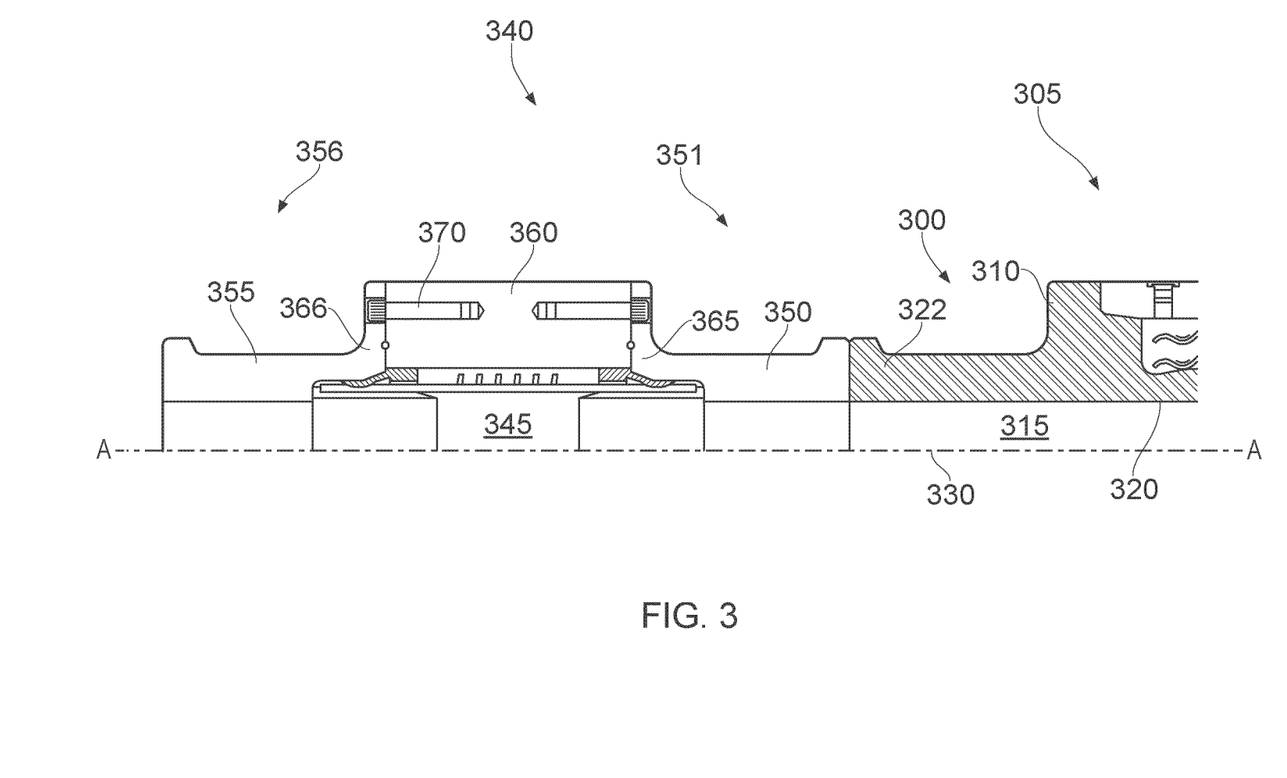
FIG. 3 illustrates a test arranged in an in-line configuration with the flexible pipe.

FIG. 3 illustrates a cross-section through one half of an end region 300 of a flexible pipe 305 which includes flexible pipe body 100 terminated in an end fitting 310. The various layers of the flexible pipe body 100 illustrated in FIG. 1 are terminated in the end fitting according to a known termination mechanism. A central bore 315 extends along the length of the flexible pipe and this bore is defined by an inner surface 320 of an innermost layer of the multi-layer flexible pipe and each end fitting.

The end fitting 310 is a rigid body having a flange 322 at one end and an open mouth at a further end defined by a flared out mouth part. A central longitudinal axis 330 of the flexible pipe is illustrated by the line A-A in FIG. 3.

Also illustrated in FIG. 3 is a test specimen 340. The test specimen 340 is thus an example of a probe specimen. That is to say, a specimen piece which can be used to probe one or more layers from the flexible pipe. When a test cycle is to be applied, the specimen is referred to as a test specimen. When a conditioning treatment cycle is to be applied, the specimen is referred to as a conditioning specimen. When a test cycle preceded by a conditioning cycle is to be applied, the specimen is referred to as a test specimen. The specimen is connected in an in-line configuration with the flexible pipe. That is to say, the test specimen 340 is connected to the flange 322 of the end fitting and the test specimen 340 has a longitudinally extending central bore 345 which is aligned on substantially the same axis 330 as the pipe bore. Aptly the central bore of the test specimen has a substantially similar or identical cross-section to that of the flexible pipe. The internal bore 345 in the test specimen 340 thus provides a generally cylindrical tube which substantially matches the dimensions of the cylindrical tube-like fluid passageway provided by the flexible pipe. By securing the test specimen 340 in an in-line configuration, the combined bore region formed by the bore 345 of the test specimen and the bore 315 of the flexible pipe can be pressurised and/or heated and/or have fluids running through it simultaneously and under identical conditions.

The test specimen 340 (which is shown in more detail in FIG. 4) has a connector 350 at a first end 351 and a further connector 355 at a further end 356. The connectors 350, 355 are substantially identical but are arranged in a mirrored (or back-to-back) configuration. Different connector designs could optionally be utilised as long as they are able to connect to an end fitting of the flexible pipe at one end and a further flexible pipe or test rig at the other. The first connector 350 is illustrated in FIG. 3 as being secured to the flange 322 of the end fitting 310 of the flexible pipe. The test specimen 340 also includes an intermediate connector 360 which is an annular body to which flanges 365, 366 on respective ends of the first and further connectors 350, 355 can be secured by bolts 370. Other securing mechanisms such as temporary welds or the like could of course be utilised.

Figure 4:
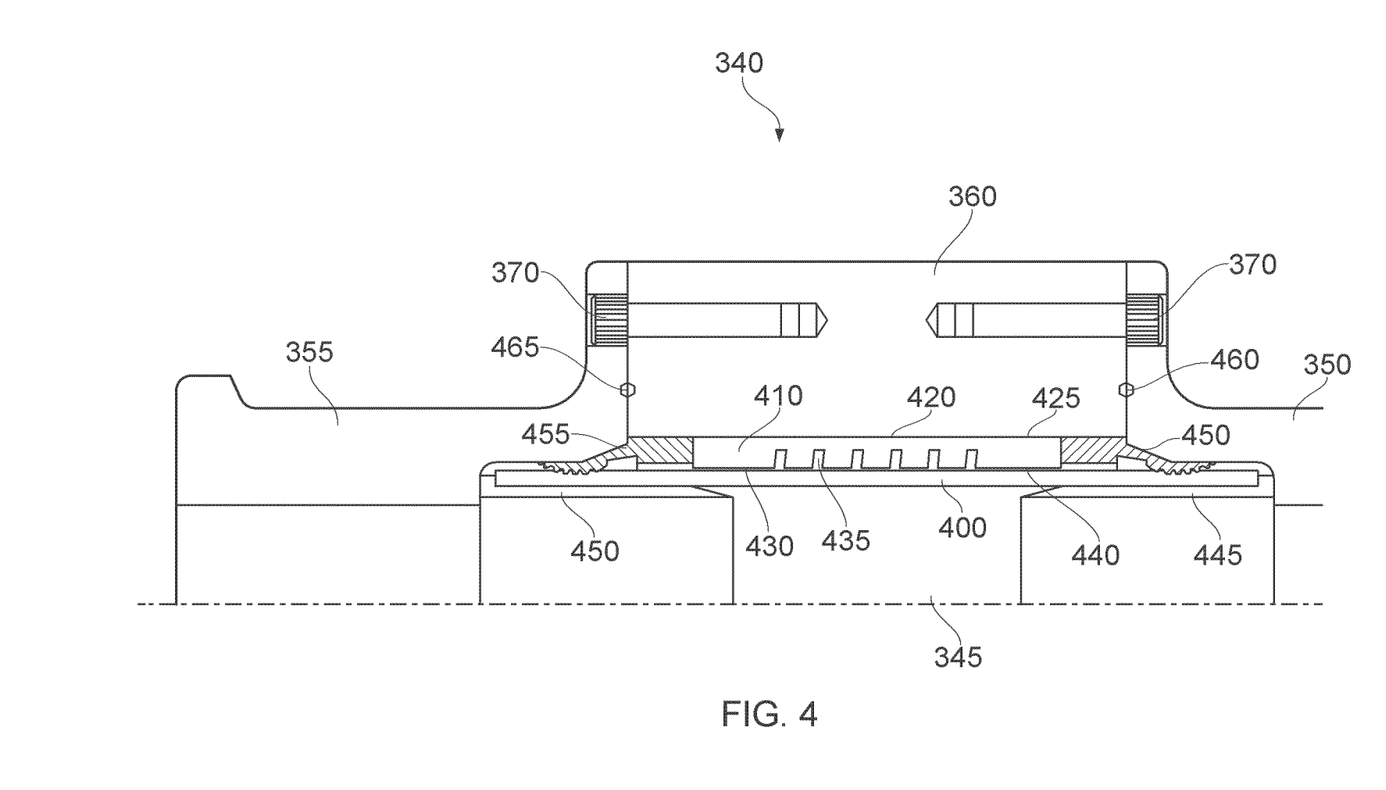
FIG. 4 illustrates a mounted test layer in more detail.

FIG. 4 illustrates the test specimen 340 in more detail. As illustrated in FIG. 4, the test specimen includes a tubular test layer 400. This is secured in place in the test specimen in such a way so that the tubular specimen layer is substantially in line with the flexible pipe. One or more test layers may be mounted in a specimen piece in an appropriate fashion. When the flexible pipe body, which forms part of the flexible pipe 305, is manufactured and before an end fitting is utilised to terminate each end of the flexible pipe body, sections of one or more layers of the flexible pipe body are removed. For example, an end section of the flexible pipe body may be cut off or one or more layers of the flexible pipe body may be manufactured over size and then cut off. In any event, one or more layers from the flexible pipe body, manufactured under identical conditions to the remainder of the flexible pipe body, can be provided in the test specimen for subsequent testing. Such layers are mounted within the test specimen 340.

FIG. 4 helps illustrate an embodiment in which a length of the layer which forms part of the internal pressure sheath 102 has been removed from the flexible pipe body. Rather than include a tubular section of a pressure armour layer, a rigid cylindrical shaped simulation piece 410 is mounted in the test specimen 340. The simulation element 410 is a hollow cylindrical element having a smooth cylindrical outer surface 420 which fits snugly against a radially innermost surface 425 of an innermost hollow region of the intermediate connector 360. A radially innermost substantially cylindrical surface 430 of the simulation element 410 is substantially smooth apart from a series of notches 435 which extend into the simulation element 410 away from where the test layer 400 is mounted. The notches may be formed as spaced apart rings on the inner surface of the simulation element or may be formed as a single helically extending groove which extends longitudinally along a portion of the inner surface of the simulation element. The notches simulate indents which would otherwise be formed by wound layers forming a pressure armour layer. Such a layer would typically lie radially outside the fluid retaining layer 400. A small gap 440 is optionally left at an interface region between the radially outermost surface of the test layer and radially innermost surface 430 of the simulation element 410.

A collar 445 is located in a first end of the tubular test layer 400 and a further collar 450 is located at the remaining end of the test layer 400. When the test layer 400 is mounted in the test specimen 340 the collars are first located within a tubular test layer which has been removed from the flexible pipe. The simulation element 410 is then located around the outer surface of the test layer and a first and further sealing ring 450, 455 likewise slid over the outer surface of the test layer. The intermediate connector 360 is then located over the simulation element and the end connectors are moved together towards the intermediate connector. First and further gaskets 460, 465 are located in corresponding grooves in the mating surfaces of the connectors and intermediate connector. As the connectors 350, 355 are secured to the intermediate connector they energise the sealing rings 450, 455 against an inner mouth of each connector 350, 355 and the inner collars 445, 450. When duly bolted together a sealed pathway is provided for fluid to flow along the bore 345 in the test specimen 340.

As illustrated in FIG. 4, the inner bore 345 of the test specimen may not be entirely perfectly smooth. Nevertheless, the test layer 400 is exposed to the pressure and fluid characteristics of any fluid flowing down the bore and likewise is exposed on a radially outer surface to the shape and configuration of a rigid layer which simulates a covering armour layer experienced by the equivalent layer in the flexible pipe. The inset regions of the notches 435 thus have a dimension and shape which at least approximates to a corresponding dimension and shape of concave regions between adjacent windings of a carcass layer for example. In this way, when a test and/or conditioning regime is carried out on the flexible pipe, the same test conditions are applied to the test layer 400. Subsequent to the test being carried out the test specimen 340 may be removed from the in-line configuration and opened up to release the test layer 400. This may then subsequently be analysed for any desired parameter which can be used to indicate acceptable or non-acceptable characteristics.

In this way, certain embodiments of the present invention provide the ability to test a section of the same pipe or a stripped down section of the same pipe or even just a single layer from the same production run of pipe. The same pressure tests and/or conditioning steps and therefore the same pressure cycle regime as the pipe itself undergoes may be experienced by the test layers. A successful evaluation subsequently for crazing or other such characteristics on a test sample from the same production run which has experienced the same pressure cycle will provide categoric evidence that the pipe itself is acceptable. This may be carried out without the need to cut and examine a completed and factory acceptance tested (FAT) section of pipe or perform a second test off-line in a different test set up.

Figure 5:
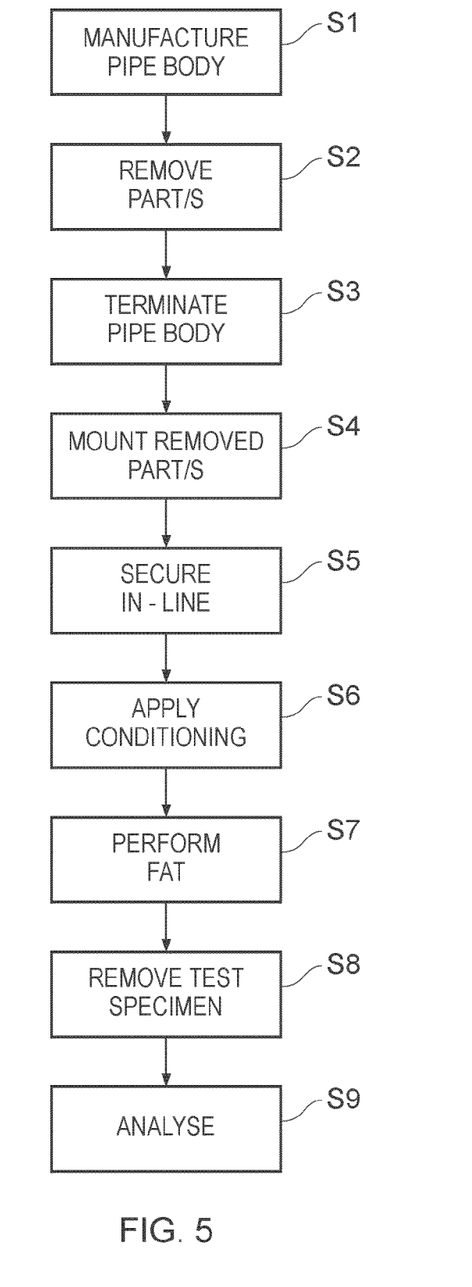
FIG. 5 illustrates a testing method.

FIG. 5 illustrates a method of conditioning and subsequently testing a flexible pipe and test specimen. At step S1 a portion of flexible pipe body is manufactured. As indicated earlier, the flexible pipe body may be a single tubular layer or may be a multi-layer structure of the type typically known as unbonded flexible pipe and in accordance with API 17J. The flexible pipe body may typically extend for a few tens of meters or even hundreds or even thousands of meters in length. In order to provide an in-line test mechanism as described hereinbefore parts of one or more layers of the flexible pipe are removed at this point. For example, an end of the manufactured flexible pipe body may be sliced off at step S2. Alternatively, extra lengths of one or more layers of the flexible pipe body may be manufactured during step S1.

These may subsequently be removed for incorporation into the test specimen as an alternative.

The remaining majority of the flexible pipe body is then terminated in one or more end fittings at step S3. This produces the flexible pipe which will ultimately be delivered to an end user and which must thus undergo an FAT.

Prior to the FAT the one or more layers of flexible pipe body which were removed at step S2 are mounted in the test specimen 340. This is illustrated in step S4. The test specimen 340 and flexible pipe 305 are then secured together in an end-to-end "in-line" configuration. This is illustrated at step S5. An optional step is illustrated at step S6 in which a conditioning routine or regime is applied to the combined length of the test specimen 340 and flexible pipe 305. For example, a treatment stage may be undertaken whereby polymeric layers in the flexible pipe are treated with pressure and heat. For example, heated water may be used to pressurise the internal bore of the pipe body and test specimen. This can be achieved by flushing heated water into the pipe body and holding the pressure for a predetermined period of time. In this manner, the pipe body is therefore subject to internal pressurisation. The heat from the heated water will conduct to the polymeric layer/s and heat the polymeric layer/s.

Step S7 illustrates the performance of a factory acceptance test (FAT) which occurs after the optional treatment/conditioning step S6. During the conditioning/treatment step S6 and the FAT step S7 an identical cycle is simultaneously applied to the one or more tubular test layers in the test specimen 340 and the flexible pipe body of the flexible pipe secured in an in-line configuration with the test specimen 340.

After the FAT carried out at step S7 the test specimen 340 is removed from its connection with the flexible pipe 305. This is illustrated as step S8. The flexible pipe 305 is thus left intact. The test specimen 340 may then be opened by removing the securing bolts 370 or other securing mechanisms and the one or more test layers 400 mounted in the test specimen 340 removed. These may then be analysed at step S9 according to known techniques to identify the existence or non-existence of potential problems. For example, analysis can be carried out to identify evidence of micro-crazing. If during this evaluation step it can be determined that the test layer/s 400 suffers from no undesired characteristics and indeed if that layer/s has desired characteristics, then a determination can be made that the layers of the flexible pipe are highly likely to be acceptable.

Aptly, according to certain embodiments of the present invention a probe cycle such as a test cycle or conditioning treatment cycle may be simultaneously applied to a flexible pipe and to a layer arranged in a specimen connected in an in-line configuration with the flexible pipe. A conditioning cycle may first be applied to both the flexible pipe and specimen and then a test cycle applied whilst the specimen and flexible pipe remain in the in-line configuration. Alternatively, subsequent to a conditioning cycle being applied with the flexible pipe and specimen in an in-line configuration, the specimen may be detached from the flexible pipe. Thereafter, the flexible pipe may be tested in one particular way and the layer of the specimen tested in a further manner.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of probing a layer of a flexible pipe, comprising the steps of:
   securing a tubular test layer and a flexible pipe together in an in-line configuration;
   applying at least a test cycle to the flexible pipe, wherein the test cycle comprises the step of applying a pressure to the layer using a pressurising medium which is at least 1.5 times a design pressure of the flexible pipe for a predetermined period of time; and
   simultaneously applying the test cycle to the tubular test layer;
   wherein said steps of securing a tubular test layer and a flexible pipe together in an in-line configuration, applying at least a test cycle to the flexible pipe and simultaneously applying the test cycle to the tubular test layer are performed prior to utilisation of the flexible pipe.

2. The method as claimed in claim 1 wherein said method comprises the step of applying a conditioning cycle to the flexible pipe and a tubular conditioning layer connected in an in-line configuration with said flexible pipe.

3. The method as claimed in claim 1, further comprising the steps of:
   prior to applying the test cycle, applying a conditioning cycle to the flexible pipe; and
   simultaneously applying the conditioning cycle to the test layer connected in said in-line configuration.

4. The method as claimed in claim 1, further comprising the steps of:
   subsequent to application of the test cycle, disconnecting the test layer from the flexible pipe leaving the flexible pipe intact; and
   determining if at least one characteristic associated with the test layer satisfies at least one pre-determined condition.

5. The method as claimed in claim 1, further comprising the steps of:
   providing the test layer by cutting off an end section from manufactured flexible pipe body and providing the cut off end section for testing.

6. The method as claimed in claim 1, further comprising the steps of:
 providing the test layer by, during manufacture of the flexible pipe body, manufacturing at least one layer having an excess length, cutting off the excess length of said one layer and providing the cut off length for testing.

7. The method as claimed in claim 1, further comprising the step of:
 when the test layer is a polymer layer, locating a pressure armour simulation element over the test layer prior to connection of the test layer in said in-line configuration with the flexible pipe.

8. The method as claimed in claim 2, further comprising the steps of:
 subsequent to applying the conditioning cycle, removing the conditioning layer from the in-line configuration and subsequently applying the test cycle to the flexible pipe.

9. The method as claimed in claim 1, further comprising the steps of:
 applying the test cycle by urging fluid having a pressure elevated with respect to an ambient pressure along an inner bore of the flexible pipe and the test layer for a pre-determined period of time.

10. The method as claimed in claim 9 whereby said step of applying a test cycle comprises applying a factory acceptance test (FAT) to the flexible pipe.

11. The method as claimed in claim 9 wherein the elevated pressure is about around 1.5 times a design pressure of the flexible pipe.

12. The method as claimed in claim 1 whereby the test layer is connected in-line with the flexible pipe by a method comprising the steps of:
 sealing a first end of the tubular test layer to a first connector;
 sealing a second end of the test layer to a second connector; and
 connecting a one of the first and second connectors to an end fitting of the flexible pipe.

13. The method as claimed in claim 12 whereby the test layer is sealed to the first connector and the second connector by a method comprising the steps of:
 locating a first inner collar member and second inner collar member at a respective end of an inner bore region of the test layer;
 locating a first sealing ring and a second sealing ring over the test layer at respective first and second ends of the test layer; and
 securing the first and second connectors to an intermediate connector body.

14. The method as claimed in claim 13, further comprising the step of:
 energising the first and second sealing rings as the first and second connectors are secured to the intermediate connector body.

15. The method as claimed in claim 13, further comprising the step of:
 sealing each connector to the intermediate body with at least one gasket ring.

16. A method of probing a layer of a flexible pipe, comprising the steps of:
 securing a tubular conditioning layer and a flexible pipe together in an in-line configuration;
 applying at least a conditioning cycle to the flexible pipe, wherein the conditioning cycle comprises the step of applying a pressure to the layer using a heated pressurising medium; and
 simultaneously applying the conditioning cycle to the tubular conditioning layer
 wherein said steps of securing a tubular conditioning layer and a flexible pipe together in an in-line configuration, applying at least a conditioning cycle to the flexible pipe and simultaneously applying the conditioning cycle to the tubular conditioning layer are performed prior to utilisation of the flexible pipe.

\* \* \* \* \*